United States Patent
Oka et al.

[11] Patent Number: 5,948,618
[45] Date of Patent: Sep. 7, 1999

[54] PRIMER FOR GENE AMPLIFICATION, METHOD FOR NUCLEIC ACID DISCRIMINATION WITH THE USE OF THE SAME, AND NUCLEIC ACID DISCRIMINATION KIT

[75] Inventors: Takanori Oka; Akio Yamane, both of Hiroshima, Japan

[73] Assignee: Wakunaga Seiyaku Kabushiki Kaisha, Osaka, Japan

[21] Appl. No.: 08/875,377

[22] PCT Filed: Jan. 26, 1996

[86] PCT No.: PCT/JP96/00151

§ 371 Date: Nov. 24, 1997

§ 102(e) Date: Nov. 24, 1997

[87] PCT Pub. No.: WO96/23077

PCT Pub. Date: Aug. 1, 1996

[30] Foreign Application Priority Data

Jan. 27, 1995 [JP] Japan ................................. 7-031477

[51] Int. Cl.[6] ............... C12Q 1/68; C07H 21/02; C07H 21/04; C12N 15/00
[52] U.S. Cl. .................. 435/6; 536/23.1; 536/24.3; 935/76; 935/77; 935/78
[58] Field of Search ............... 435/6; 536/23.1, 536/24.3; 935/76, 77, 78

[56] References Cited

U.S. PATENT DOCUMENTS

| | | | |
|---|---|---|---|
| 5,104,792 | 4/1992 | Silver et al. | 435/6 |
| 5,106,727 | 4/1992 | Hartley et al. | 435/6 |
| 5,629,158 | 5/1997 | Uhlen | 435/6 |
| 5,688,643 | 11/1997 | Oka et al. | 435/6 |

OTHER PUBLICATIONS

Terouanne et al. (or Nicolas et al.), Analytical Biochemistry 205 : 193 (1992).

Oka et al., Nucleic Acids Research 22 (9) : 1541–1547 (1994).

Ubukata et al., J. of Clinical Microbiology 30 : 1728–1733 (1992).

Verrhasselt et al., DNA Sequence 2 :281–287 (1992).

Yamane et al., Nucleic Acids Research Symposium Series No. 20, pp. 91–92 (1988).

The Stratagene Catalog, p. 39 (1988 Edition).

Matthews et al., Analytical Biochemistry 169 : 1–25 (1988).

Innis et al., "PCR Protocols: A Guide to Methods and Application", pp. 84–91 and 909–112, Academic Press, San Diego, CA (1990).

*Primary Examiner*—W. Gary Jones
*Assistant Examiner*—Ethan Whisenant
*Attorney, Agent, or Firm*—Birch, Stewart, Kolasch & Birch, LLP

[57] ABSTRACT

A nucleic acid differentiation method utilizing complementary strand-exchange reaction in competitive hybridization can clearly differentiate a site of gene mutation or a difference between genes in a target nucleic acid even when the gene mutation or difference is located near the primer binding site of the target nucleic acid.

The invention provides a method and assay kit for differentiating the identity between two nucleic acids by labeling a gene amplifying primer including a primer main region which is complementary to the target nucleic acid to be amplified and having added to the 5' end of the primer main region a sequence which is noncomplementary to the target nucleic acid; amplifying one of two nucleic acids to be determined for identity using the labeled primer, thereby obtaining a labeled DNA; mixing the labeled DNA with an unlabeled DNA prepared from the other nucleic acid to effect competitive hybridization; and measuring the degree of complementary strand-exchange that has occurred between the labeled DNA and the unlabeled DNA by utilizing the label.

14 Claims, 2 Drawing Sheets

```
                    SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
         (A) LENGTH: 21 base
pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc
= "Primer"

(xi) SEQUENCE DESCRIPTION: SEQ ID NO:1:

GTTTCTTGGA GCAGGTTAAA C

21

(2) INFORMATION FOR SEQ ID NO:2:

(i) SEQUENCE CHARACTERISTICS:
         (A) LENGTH: 20 base
pairs
         (B) TYPE: nucleic acid
```

(C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:2:

CCGCTGCACT GTGAAGCTCT

20

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:3:

TTATTTATTT TATTTTTATT CCGCTGCACT GTGAAGCTCT

40

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:4:

CCCGCCGCGC CCCGCCCCCG CCGCTGCACT GTGAAGCTCT

40

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:5:

GTAAGTGGGT AGTCTTGAGC CCGCTGCACT GTGAAGCTCT

40

(2) INFORMATION FOR SEQ ID NO:6:

(i) SEQUENCE CHARACTERISTICS:
        (A) LENGTH: 20 base pairs

```
            (B) TYPE: nucleic acid
            (C) STRANDEDNESS: single
            (D) TOPOLOGY: linear (ii) MOLECULE TYPE: other nucleic acid
            (A) DESCRIPTION: /desc
= "PRIMER"

(xi) SEQUENCE DESCRIPTION: SEQ ID NO:6:

TTCTTGGAGT ACTCTACGTC
```

PRIMER FOR GENE AMPLIFICATION, METHOD FOR NUCLEIC ACID DISCRIMINATION WITH THE USE OF THE SAME, AND NUCLEIC ACID DISCRIMINATION KIT

FIELD OF THE INVENTION

The present invention relates to a gene amplifying primer, a nucleic acid-differentiation method and a nucleic acid-differentiation assay kit using such primer. More specifically, the present invention relates to a gene amplifying primer which permits a target nucleic acid to be amplified, even when the target nucleic acid has a site of gene mutation or a difference among genes located in the vicinity of a primer binding site thereof, such that the site of gene mutation or difference may be shifted to the central side; a nucleic acid-differentiation method which ensures to detect a site of gene mutation or difference among genes in a target nucleic acid using the primer even when the site of gene mutation or difference is located near the primer binding site of the target nucleic acid; and a nucleic acid-differentiation assay kit for assaying genes by this nucleic acid-differentiation method.

BACKGROUND OF THE INVENTION

Recent years have brought amazing progress in the areas of molecular biology and genetics. The findings accumulated in such fields have not only contribution to the chemical and physical elucidation of biological phenomena, but also great influence on the human being, especially on medical science and practice. As a consequence, the DNA medicine, which started from DNA investigation, is marking great steps toward clinical fields far beyond the expectation. As it is recently revealed that almost all diseases are related to DNA, diagnosis at gene level is gradually regarded to be indispensable.

It is believed that those diseases now generally referred to as gene diseases (molecular diseases) include almost all of the enzyme deficiencies which are long known as diseases caused by inborn errors of metabolism. Detection of gene mutation is quite effective for the diagnosis of such gene diseases.

When a large number of genotypes are present as in the case of human leukocyte antigen (HLA), which hold the key to success of bone marrow transplantation or organ transplantation, it is desired to conveniently and rapidly determine the gene type at a high specificity.

An exemplary method for detecting the gene mutation or determining the gene type is the method of Nicolas, J. C. et al. (EP-A 362042; Anal. Biochem. 205, 193 (1992)), which is a modification of ED-PCR detection system (Japanese Patent Application Kokai (JP-A) Nos. 314965/1989 and 252300/1989; J. Clin. Microbiol. 30, 1728 (1992)).

The method of Nicolas et al. is carried out as follows. First, a labeled standard DNA is prepared from a double stranded nucleic acid fragment including a mutation region to be detected by introducing biotin label in one strand and FITC label in the other strand of the nucleic acid fragment. The labeled standard DNA is then mixed with an excess amount of a sample DNA including an unlabeled nucleic acid fragment of the same region as the standard DNA, and the mixture is heated for denaturation and slowly cooled (competitive hybridization). When a fragment including a nucleotide sequence identical with that of the labeled standard DNA is present in the sample, strand exchange would occur between the double stranded labeled standard DNA and the double stranded sample DNA, resulting in the amount of the labeled standard DNA possessing both the biotin label and the FITC label being reduced from the initial amount. On the other hand, when a fragment including a nucleotide sequence which is partly different from that of the labeled standard DNA is present in the sample, strand exchange is unlikely to occur between the double stranded labeled standard DNA and the double stranded sample DNA and the initial amount of the labeled standard DNA would remain substantially unchanged. Briefly stated, this method determines whether or not a fragment including a nucleotide sequence identical with that of the labeled standard DNA is present, by observing a change of the initial amount of the labeled standard DNA added through the steps of mixing, denaturation and annealing (competitive hybridization).

Also, the inventors of the present invention proposed a nucleic acid-differentiation method which is an improvement over the method of Nicolas et al. (PCT/JP94/01106, Nucl. Acids. Rec. 22, 1541 (1994)). In this method, a primer including a detectable label and a site capable of binding with a solid phase carrier is used for the PCR amplification of a target nucleic acid to produce a labeled DNA (sample DNA); and contrary to the above-described method of Nicolas et al., at least an equimolar amount of unlabeled DNA specimen of the same region (standard DNA) is added to the thus obtained labeled DNA (sample DNA) for competitive hybridization. The degree of complementary strand exchange between said sample DNA and said standard DNA is measured utilizing said detectable label and said site capable of binding with the solid phase carrier, to thereby determine the identity of nucleic acids. This method enables detection of a minute amount of mutant gene and detection of the mutation present on only one of allele, which are difficult with the above-referred method of Nicolas et al., and further can detect the proportion of such mutation.

The nucleic acid-differentiation methods of detecting gene mutation or the like by employing the detection system of ED-PCR and combining it with competitive hybridization, inclusive of the method of Nicolas et al. and the method proposed by the present inventors, are generally referred to as PCR-PHFA, hereinafter.

When gene mutation is detected by the PCR-PHFA, the primer-binding site in the nucleotide sequence may be adequately selected, and a number of primers may be prepared from which the most suitable primer is selected.

The choice of the primer-binding site, however, would be limited when the information on the nucleotide sequence is limited, or when the sequence to be amplified is common to several genes. For example, in the case of determining the HLA type or the like, DNAs of various types should be amplified with one pair of primers for the sake of examination efficiency, and consequently, the choice of the primer binding sequence is limited to the sequence commonly found among the different DNA types. As a consequence, the site of nucleotide difference between particular types of DNAs can be situated quite near the primer binding site. Continuing further investigations, the present inventors found that, in such case, the nucleotide (sequence) to be differentiated is located near the terminal of the PCR amplification product and sometimes difficult to differentiate with the above-described PCR-PHFA.

DISCLOSURE OF THE INVENTION

The present invention has been made in consideration of the above-mentioned situation, and an object of the present invention is to provide a nucleic acid-differentiation method which ensures detection of mutation in a target nucleic acid and differentiation of genes for identity even when the target nucleic acid has the mutation site or the nucleotide sequence to be differentiated near the primer binding site, and a gene amplifying primer and a nucleic acid-differentiation assay kit for use in the practice of the differentiation method.

In order to achieve the above object, the present inventors made an extensive investigation to solve the problem that nucleic acid differentiation based on the above-described PCR-PHFA is easy when a mutation site or a nucleotide sequence to be differentiated is located near the center of an amplified product, but difficult when such site is located near the end of the amplified product.

Figure 1:
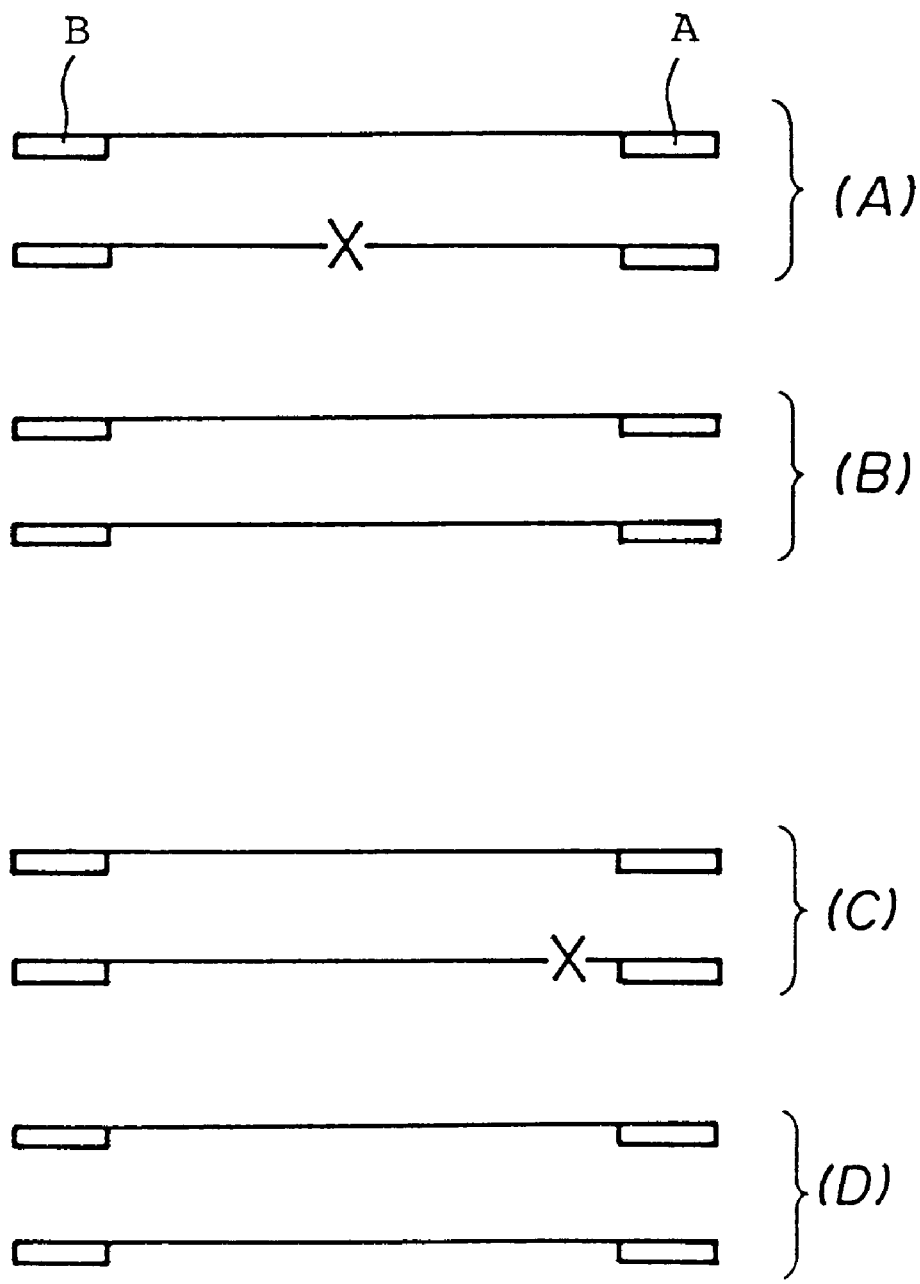
FIG. 1 is a schematic view for explaining the difference in stability in competitive hybridization depending on whether a site of mutation is located in a central portion or end portion of DNA.

After such investigation, it was estimated that, as depicted in FIG. 1, in the competitive hybridization, when the mutation site or the nucleotide sequence to be differentiated is located in the central portion of the DNA strand, the difference in stability is significant between the double stranded fragment (A) including the mismatch site and the fully complementary double stranded fragment (B), while the difference in stability is less significant between the double stranded fragment (C) including the mismatch site and the fully complementary double stranded fragment (D) when the mutation site or the nucleotide sequence to be differentiated is located in the end portion of the DNA strand, rendering the differentiation difficult. On the basis of such estimation, it was further estimated that, if the difference in stability between (C) and (D) could be enlarged, the differentiation between (C) and (D) would become easier to enable a convenient differentiation even if the nucleic acid includes the mutation site or the nucleotide sequence to be differentiated near its primer binding site. It should be noted that, in FIG. 1, A and B designate the primers.

In view of such situation, the inventors of the present invention have made further investigation and found that, in the amplification of the target nucleic acid including the mutation site or the nucleotide sequence to be differentiated near its primer binding site, if a length of sequence that is noncomplementary to the target nucleic acid is added on the 5' terminal of the main region of the amplification primer, the amplification product obtained will be the one wherein the mutation site or the nucleotide sequence to be differentiated has shifted to the central side; and when the differentiation by competitive hybridization in accordance with the above-described PCR-PHFA is carried out using the thus obtained amplification product, the gene mutation or the nucleotide sequence to be differentiated can be easily differentiated. The present invention has been completed on the basis of such finding.

Figure 2A:
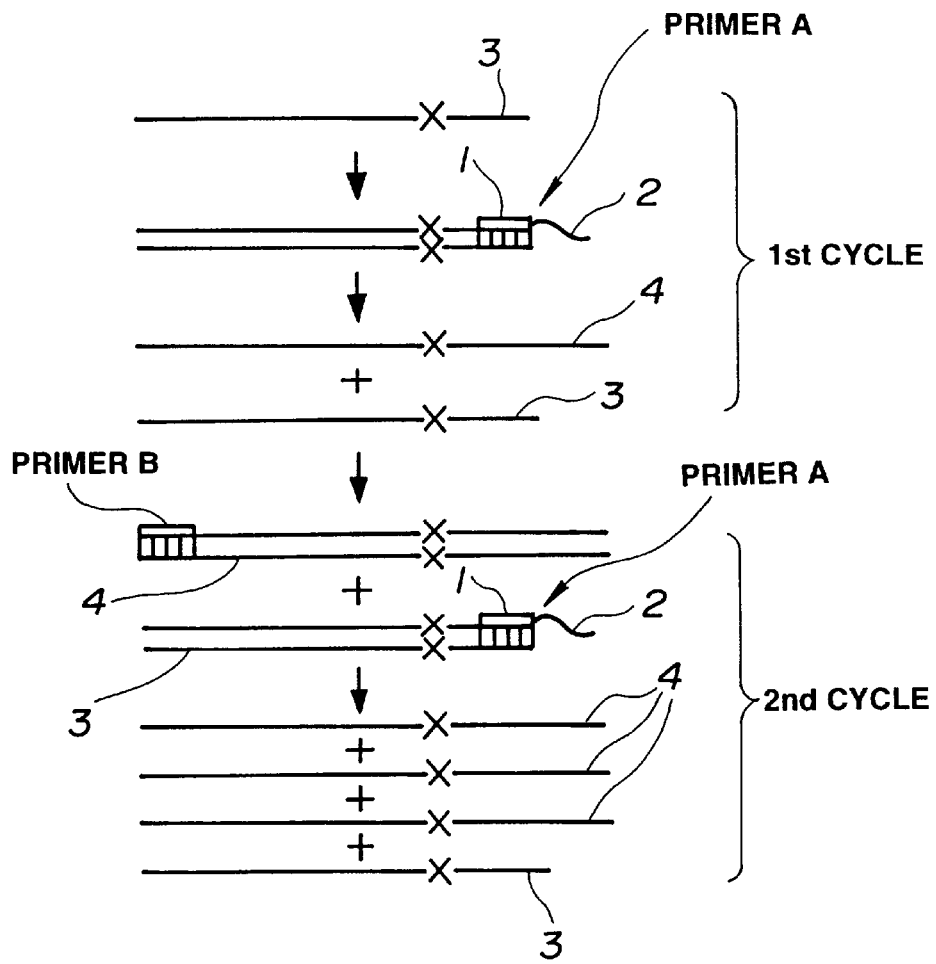
FIGS. 2(A) and 2(B) schematically shows the principle of the present invention. (A) is a schematic view for explaining the principle of gene amplification using the primer of the present invention. (B) is a schematic view for explaining the principle of competitive hybridization.
Figure 2B:
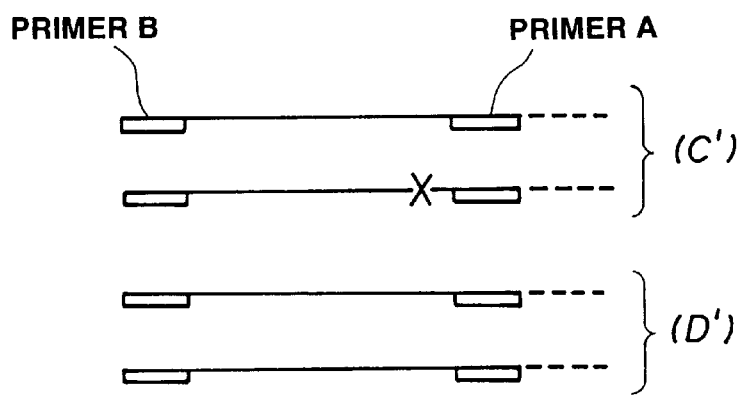

More illustratively, as shown in FIG. 2(A), when the target nucleic acid 3 including the mutation site or the nucleotide sequence to be differentiated (hereinafter referred to as the mutation site or the like) X near its primer binding site is amplified with a primer A comprising a primer main region 1 complementary to the target nucleic acid having added to its 5' end an additional sequence 2 that is non-complementary to the target nucleic acid, one amplification product 4 wherein the mutation site or the like X has shifted to the central side and one target nucleic acid 3 will be obtained in the reaction of the first cycle. In the reaction of the second cycle, the amplification product 4 will produce two similar amplification products 4 through the use of another primer B which is complementary to the target nucleic acid, and the target nucleic acid 3 will produce one similar amplification product 4 through the use of the primer A, resulting in three similar amplification products 4 in total. The amplification product 4 wherein the mutation site or the like X has shifted to the central side will be further amplified by repeating similar cycles. When the amplification product 4 is used as a sample DNA, and the mutation site or the like X is determined by the above-described PCR-PHFA, as depicted in FIG. 2(B), in the case of the fully complementary double stranded fragment (D'), the number of hydrogen bonds serially present along the strand will be increased to result in the increased stability in contrast to the case of the double stranded fragment (C') including the mismatch site wherein the stability remains unchanged in spite of the addition of the additional sequence on the 5' end of the primer A on the side of the mutation site or the like X since the stability of the molecule is determined by the longest length of the serially present hydrogen bonds, namely, the length between the mutation site or the like X and the primer B on the side remote from the mutation site or the like X. As a consequence, the difference in stability between the fully complementary double stranded fragment (D') and the double stranded fragment (C') including the mismatch site is enlarged to enable a convenient differentiation of the mutation site or the like X. The present invention has been completed on the basis of such finding.

Accordingly, the present invention provides a gene amplifying primer for use in DNA differentiation wherein the DNA differentiation is effected by utilizing a complementary strand-exchange reaction in competitive hybridization, characterized in that said primer comprises a primer main region which is complementary to a target nucleic acid to be amplified and a sequence added to the 5' end of the primer main region which is noncomplementary to the target nucleic acid.

In this regard, a detectable label and/or a site capable of binding to a solid phase carrier may be introduced into the gene amplifying primer according to the present invention so that the gene amplification product produced by using the amplifying primer may be subject to the differentiation method based on competitive hybridization (PCR-PEFA) as a labeled DNA.

The present invention also provides methods for differentiating nucleic acids by using the above-mentioned gene amplifying primer according to the present invention, which are:

(1) a nucleic acid differentiation method for differentiating a gene in a predetermined region of a target nucleic acid in a sample, characterized in that said method comprises the steps of amplifying the predetermined region of the target nucleic acid in the sample by using a pair of primers comprising a primer having introduced therein a detectable label and a primer having introduced therein a site capable of binding to a solid phase carrier, at least one of said primers being the above-described gene amplifying primer according to the present invention having introduced therein a detectable label and/or a site capable of binding to a solid phase carrier; using the resulting labeled DNA as a labeled sample DNA and using an unlabeled DNA specimen to be determined for identity with said labeled sample DNA as an unlabeled standard DNA; adding an equimolar amount or excess of said unlabeled standard DNA to said labeled sample DNA to carry out competitive hybridization; and thereafter measuring the degree of complementary strand-exchange that has occurred between said labeled sample DNA and said unlabeled standard DNA by utilizing said detectable label and said site capable of binding to the solid phase carrier to thereby determine the identity between the nucleic acids; and (2) a nucleic acid differentiation method for differentiating a gene in a predetermined region of a target nucleic acid in a sample, characterized in that said method comprises the steps of amplifying a DNA specimen by using a pair of primers comprising a primer having introduced therein a detectable label and a primer having introduced therein a site capable of binding to a solid phase carrier, at least one of said primers being the above-described gene amplifying primer according to the present invention having introduced therein a detectable label and/or a site capable of binding to a solid phase carrier; using the resulting labeled DNA as a labeled standard DNA and using an unlabeled DNA in the predetermined region of the target nucleic acid in the sample to be determined for identity with said labeled standard DNA as an unlabeled sample DNA; adding an equimolar amount or excess of said unlabeled sample DNA to said labeled standard DNA to carry out competitive hybridization; and measuring the degree of complementary strand-exchange that has occurred between said labeled standard DNA and said unlabeled sample DNA by utilizing said detectable label and said site capable of binding to the solid phase carrier to determine the identity between the nucleic acids.

In such case, the unlabeled standard DNA in the above-mentioned differentiation method (1) and the unlabeled sample DNA in the above-mentioned differentiation method (2) may be prepared by using the gene amplifying primer according to the present invention which has not introduced therein a detectable label or a site capable of binding to a solid phase carrier; or by gene cloning using a vector selected from a plasmid vector, a phage vector, and a chimerical vector of a plasmid and a phage.

Furthermore, the present invention provides an assay kit for effecting nucleic acid differentiation by the above-mentioned nucleic acid differentiation method (1), characterized by comprising a pair of primers for preparing a labeled sample DNA comprising a primer having introduced therein a detectable label and a primer having introduced therein a site capable of binding to a solid phase carrier, wherein at least one of the primers is the above-described gene amplifying primer according to the present invention having introduced therein a detectable label and/or a site capable of binding to a solid phase carrier; and one of the following (A) to (C):
 (A) an unlabeled DNA specimen,
 (B) a pair of primers for preparing an unlabeled DNA specimen wherein at least one of said primers comprises the gene amplifying primer according to the present invention which does not have a detectable label or a site capable of binding to a solid phase carrier introduced therein, and
 (C) a vector for preparing an unlabeled DNA specimen selected from a plasmid vector, a phage vector, and a chimeric vector of a plasmid and a phage; and an assay kit for effecting nucleic acid differentiation by the above-mentioned nucleic acid differentiation method (2), characterized by comprising a pair of primers for preparing a labeled standard DNA comprising a primer having introduced therein a detectable label and a primer having introduced therein a site capable of binding to a solid phase carrier, wherein at least one of the primers is the above-described gene amplifying primer according to the present invention having introduced therein a detectable label and/or a site capable of binding to a solid phase carrier; and one of the following (A) and (B):
 (A) a pair of primers for preparing an unlabeled sample DNA wherein at least one of said primers comprises the gene amplifying primer according to the present invention which does not have a detectable label or a site capable of binding to a solid phase carrier introduced therein, and
 (B) a vector for preparing an unlabeled sample DNA selected from a plasmid vector, a phage vector, and a chimeric vector of a plasmid and a phage.

The above-mentioned nucleic acid differentiation assay kits of the present invention are adapted for assaying nucleic acids by the above-mentioned nucleic acid differentiation methods (1) and (2), respectively. When the differentiation assay is carried out by using the former assay kit in accordance with the above-mentioned method (1), the target nucleic acid in the sample is amplified with a pair of labeled primers to prepare labeled sample DNA, and competitive hybridization is carried out between the thus prepared labeled sample DNA and the unlabeled DNA specimen; and when the differentiation assay is carried out by using the latter assay kit in accordance with the above-mentioned method (2), the DNA specimen is amplified with a pair of labeled primers to prepare labeled standard DNA, and competitive hybridization is carried out between the thus prepared labeled standard DNA and the unlabeled sample DNA prepared from the sample using the unlabeled primer or vector; and in either case, the resulting hybridization products are measured by utilizing the label. In either case, in amplifying the target nucleic acid with the primers, the sample is subjected to an adequate pretreatment such as cell disruption, if desired; and reagents necessary for the amplification are employed. The measurement of the hybridization product is carried out by trapping the hybridization product on a solid phase carrier with the use of the site capable of binding to the carrier, and detecting the trapped hybridization product with the use of the detectable label. In such case, the above-mentioned nucleic acid differentiation assay kit of the present invention may be constituted by incorporating the reagents and components which have been used in conventional PCR-PHFA, for example, such as the reagent for cell disruption, the reagents for nucleic acid amplification, the carrier for trapping the hybridization product, and the like.

Best Mode for Carrying Out the Invention

The present invention is described in further detail. As described above, the gene amplifying primer of the present invention comprises a primer main region complementary to the target nucleic acid having added to its 5' end a sequence which is noncomplementary to the target nucleic acid. The sequence added to the primer main region is not limited to any particular sequence so long as the sequence is non-complementary to the target nucleic acid and the sequence added does not bind to the target nucleic acid. The sequence added, however, is preferably a sequence wherein 50% or more of the constituent bases comprise guanine (G) and cytosine (C), and more preferably, a sequence wherein all of the constituent bases comprise G and/or C, since the bond between G and C is stronger than the bond between A and T due to the number of the hydrogen bonds present between the bases (three hydrogen bonds are formed between G (guanine) and C (cytosine) in contrast to two hydrogen bonds formed between A (adenine) and T (thymine)). In the nucleic acid differentiation assay, this brings a larger difference in stability between the fully complementary double stranded fragment and the double stranded fragment including the mismatch site, facilitating differentiation of the mutation or the like.

The noncomplementary sequence added is not particularly limited in length. The length, however, is preferably from 10 to 40 bases, and more preferably, from 20 to 40 bases. The noncomplementary sequence with a length of less than 10 bases might be insufficient in shifting the mutation site of the nucleic acid to the central side. A length of more than 40 bases might adversely affect the specificity of the PCR.

Furthermore, the primer of the present invention may have introduced therein either or both of a detectable label and a site capable of binding to a solid phase carrier. The introduction site of the detectable label or the site capable of binding to a solid phase carrier is not particularly limited so long as the efficiency of the primer extension reaction is not impaired, and preferably, the introduction site is an active group in a hydroxyl group, base or phosphate diester moiety near the 5' end.

The above-mentioned detectable label and the site capable of binding to a solid phase carrier are utilized when the primer of the present invention is used for the amplification of the target nucleic acid and the amplification product is subjected to competitive hybridization for nucleic acid differentiation. The above-mentioned detectable label may be either radioactive or radio-inactive, and preferably, radio-inactive. Exemplary radio-inactive labels include directly detectable labels such as fluorescent substances, e.g., fluorescein derivatives (fluorescein isothiocyanate etc.), rhodamine and its derivatives (tetramethylrhodamine isothiocyanate etc.), chemiluminescent substances (e.g., acridine), and delayed fluorescent substances (DTTA, manufactured by Pharmacia).

In the nucleic acid differentiation method, the label may be indirectly detected if the label is used in combination with a substance that specifically binds to the label, and such a substance may be introduced in the primer of the present invention. The label that can be used in this embodiment includes biotin, a ligand, a nucleic acid or protein of a particular type, and a hapten. Biotin may be used in combination with avidin or streptoavidin that specifically binds to biotin; and the hapten may be used with an antibody that specifically binds to the hapten. The ligand may be used with a receptor, and the nucleic acid or protein of the particular type may be used with a nucleic acid that specifically binds thereto, a nucleic acid-binding protein or a protein that has an affinity to the particular protein. Examples of the hapten that can be used include compounds having a 2,4-dinitrophenyl (DNP) group and digoxigenin, and biotin or a fluorescent substance may also be used as the hapten. The labels as described above may be introduced alone or, if desired, in combination of two or more by known means (see JP-A 59-93099, 59-148798, and 59-204200). It should be noted that the detectable label and the site capable of binding to a solid phase carrier may be the same.

The gene amplifying primer of the present invention is used for nucleic acid amplification reaction, and most preferably, in a nucleic acid differentiation method wherein PCR-PHFA utilizing ED-PCR is adopted for the detection system. In such case, the nucleic acid differentiation by PCR-PHFA may be effected either by the method (of Nicolas et al.) wherein an excessive amount of unlabeled sample DNA is mixed with labeled standard DNA, or by the method (of PCT/JP94/01106, Nucl. Acids. Rec. 22, 1541 (1994)) proposed by the inventors of the present invention wherein an excessive amount of unlabeled standard DNA is mixed with labeled sample DNA, or alternatively, by any desired competitive hybridization process involving nucleic acid amplification reaction. The mutation or the like of the target nucleic acid can be positioned near the primer binding site, in particular, when the sequences of the target nucleic acid in the regions on opposite ends are unknown, when an appropriate sequence is absent on the template DNA, and when the primer site for PCR amplification can not be changed. In such a case, the primer of the present invention may be used to enable efficient nucleic acid differentiation assay. In other words, the use of the primer of the present invention enables convenient differentiation of the mutation or the like near the primer which was difficult to differentiate in the prior art.

As described above, both the method of Nicolas et al. and the nucleic acid differentiation method previously proposed by the inventors of the present invention may be suitably used in the differentiation of the nucleic acid using the gene amplifying primer of the present invention. Particular use of the method of the present inventors, however, would enable determination of the presence/absence of a particular mutation at a non-predetermined site on a particular gene, detection of a small amount of abnormal cells with a mutant gene which are co-present with normal cells, and determination for identity of a particular gene in a plurality of samples in addition to the determination of the DNA type of the HLA gene or the like. The use of the gene amplifying primer of the present invention also enables a clear differentiation of the nucleic acid even when the mutation or the like is present near the primer binding site, thereby realizing differentiation assay with a quite high accuracy. In the following description, explanation is made for this differentiation method. In the following description, the difference in nucleotide sequences to be differentiated is generally referred to as "mutation" for simplicity.

As described above, this method is previously proposed by the inventors of the present invention, and the method comprises the steps of amplifying a particular region of a target nucleic acid in a sample by using a pair of the primers according to the present invention having a detectable label introduced in one primer and a site capable of binding to a solid phase carrier on the other primer, using the resulting labeled DNA as a sample DNA using an unlabeled DNA specimen to be determined for identity with the sample DNA as a standard DNA; adding an equimolar amount or excess of said standard DNA to said sample DNA to promote competitive hybridization; and evaluating the degree of complementary strand exchange that has occurred between said sample DNA and said standard DNA by utilizing said detectable label and said site capable of binding to the solid phase carrier, thereby determining the identity of the nucleic acid.

In this differentiation method, by adding an equimolar amount or excess, namely, an excessive amount of said unlabeled standard DNA to said labeled sample DNA, not only the detection of the occurrence of an unspecified mutation in a particular gene region, but also the determination of whether such mutation has occurred on both alleles or only on one of the alleles are enabled. Such determination is possible even when the occurrence of the mutant gene is as low as about 10%, and evaluation of the occurrence is also enabled. Furthermore, by using one DNA sample for the labeled sample DNA and the other for the unlabeled standard DNA, this differentiation method can determine the homology between genes of a particular type in two DNA samples, whether the genes in two DNA samples are identical, completely different, or partly different from one another, and a degree of difference.

According to the present invention, the gene amplifying primer of the present invention as described above is used in such nucleic acid differentiation method for at least one of the primer pair for amplification of said target nucleic acid comprising the primer having introduced therein a detectable label and the primer having introduced therein a site capable of binding to a solid phase carrier.

In the nucleic acid differentiation method of the present invention, a particular region of the target nucleic acid in the sample is amplified by using the primer of the present invention as described above for at least one of the primer having introduced therein a detectable label and the primer having introduced therein a site capable of binding to a solid phase carrier.

In such a case, both primers used for the gene amplification may comprise the primer of the present invention. It is, however, typical to constitute one primer from the primer of the present invention, and the other primer from a conventional primer solely comprising the sequence complementary to the target acid. The detectable label and the site capable of binding to a solid phase carrier introduced in the primer of the present invention and the other primer may be the same as those described in the foregoing.

The samples that may be used include blood, diseased tissue pieces, and excreta such as feces and urine available from human being. In the case of prenatal diagnosis, fetal cells in the amniotic fluid and blastomeres in a test tube may be used as the sample. The samples as such or after optional concentration into a precipitate by centrifugation may be previously subjected to cell disruption by enzymatic treatment, heat treatment, surfactant treatment or ultrasonication or a combination thereof. In this case, the cell disruption is carried out for the purpose of exposing the DNA originating from the target tissue. The cell disruption may be typically carried out in accordance with well-known processes in the literature, for example, PCR Protocols, Academic Press Inc., p 14 and p 352 (1990). Preferably, the amount of the DNA in the sample is approximately 1 to 100 $\mu$g in total. Sufficient amplification is possible with less than 1 $\mu$g of DNA.

When the primer pair for nucleic acid amplification as described above is added to the above-described sample, gene amplification through primer extension will proceed if the target nucleic acid to be amplified is present in the sample. The gene amplification may be effected by well-known PCR, LCR, 3SR, SDA and other processes (Manak, DNA Probes, 2nd Edition, p 255–291, Stockton Press, 1993), and most preferably, by PCR.

The primer extension reaction is effected by incorporating 4 types of nucleoside triphosphate (deoxyadenosine triphosphate, deoxyguanosine triphosphate, deoxycytidine triphosphate and deoxythymidine triphosphate, a mixture of which is sometimes referred to as dNTPs) as substrates into the primer.

In the extension reaction, an amplification reaction reagent including the above-mentioned nucleic acid units for amplifying nucleic acid strands and nucleic acid extension enzyme is generally employed. The nucleic acid extension enzymes incorporated in such reaction reagent include DNA polymerases such as E. coli DNA polymerase I, Krenow fragment of the E. coli DNA polymerase I, T4 DNA polymerase, and the like, and use of a thermally stable DNA polymerase such as Taq DNA polymerase, Tth DNA polymerase, Vent DNA polymerase or the like is most preferable. By using such DNA polymerase, the specificity of target sequence recognition by the primer is improved to enable rapid, specific gene amplification (For further detail, see JP-A 314965/1989 and 252300/1989). In such reaction, an oil may be added to the reaction solution to prevent evaporation of water from the reaction solution. Any oil exhibiting partition with water and having a lower specific gravity than water may be used for such purpose, and exemplary oils include silicone oil and mineral oil.

The target nucleic acid in the sample may be efficiently amplified by repeating extension reaction using the above-described nucleic acid amplification primers. The conditions and other detailed procedures of the gene amplification reaction may be adequately determined in accordance with known procedures described in the publications such as Jikken Igaku (Experimental Medicine), Yodo-sha, 8, No. 9 (1990) and PCR technology, Stockton Press (1989).

Next, competitive hybridization is effected by using the amplification product of the above-described gene amplification procedure, namely, the labeled DNA for the sample DNA, and adding the standard DNA, namely, the unlabeled DNA specimen to be determined for identity with the sample DNA to the sample DNA.

In this case, the unlabeled standard DNA is the DNA which has a sequence homologous to the amplification product of the gene whose mutation is to be detected, and in general, the unlabeled standard DNA is preferably the normal gene corresponding to the gene whose mutation is to be detected, although genes other than such normal gene may be used depending on the purpose of the detection. Such an unlabeled standard DNA may be prepared as will be described below. It should be noted that the terminology "a sequence homologous to the amplification product of the gene whose mutation is to be detected" designates the sequence which substantially shares the sequence other than the mutation site, and therefore, the sequence whose length is substantially the same.

The unlabeled standard DNA may be prepared by the amplification of the normal gene using the unlabeled primer having the same nucleotide sequence as the primer used for the amplification of the gene whose mutation is to be detected. The thus amplified gene can be further mass-produced by incorporating the gene in a vector selected from a plasmid vector, a phage vector, and a chimera vector of a plasmid and a phage, and introducing the vector in a host such as a bacterium, for example, E. coli and Bacillus subtitles or yeast (gene cloning). Alternatively, the unlabeled standard DNA may be prepared by enzymatic cleavage from a natural gene without utilizing gene amplification. Preparation by chemical synthesis is also possible in some situation.

The unlabeled standard DNA previously prepared as described above is subjected to competitive hybridization together with the labeled sample DNA as described above. In the competitive hybridization, both of the above-described DNA must be denatured, and the denaturation may be effected with heat or alkaline. The DNAs may be mixed immediately before the denaturation or after the denaturation of respective DNAs. In the method of the present invention, an equimolar amount or excess of the unlabeled standard DNA should be added to the labeled sample DNA, and generally, an amount of approximately 5 to 20 times in excess of the unlabeled standard DNA is preferably added to the labeled sample DNA. The optimal amount added, however, may vary depending on the length, base sequence, and degree of mutation of the DNA.

In the competitive hybridization, the salt concentration of the reaction solution should be adjusted to the optimal level primarily determined by the strand length. The solutions generally used in competitive hybridization are SSC (20× SSC: 3M sodium chloride; 0.3M sodium citrate) and SSPE (20×SSPE: 3.6M sodium chloride, 0.2M sodium phosphate, 2 mM EDTA), and these solutions may be used in the present invention after diluting the solution to the desired concentration. Addition of about 10% of an organic medium such as formamide or dimethylformamide may facilitate the adjustment of the solution to optimal conditions.

Competitive hybridization may be carried out by mixing the DNAs that have been denatured by the above-described procedure, and gradually reducing the temperature from the elevated temperature. With respect to temperature conditions, optimal conditions may be suitably set in accordance with the length and the sequence of the DNA to be hybridized and the difference between the mutant nucleotide sequence and the normal nucleotide sequence. Usually, the temperature conditions are set so that the temperature is reduced in the range of from 98 to 58° C. at a rate of 1° C. per 6 to 10 minutes.

Next, the product of the competitive hybridization is measured by the principle of ED-PCR (see JP-A 314965/1989 and 252300/1989 and J. Clin. Microbiol., 30, 1728 (1992), for example). In the ED-PCR, the presence of double stranded nucleic acid is indicated by a signal only when different labels are present on respective strands of the nucleic acid (The labels on the strands of the nucleic acid are the same as the case may be). Accordingly, the competitive hybridization products as described above will produce a weaker signal with an increasing strand exchange frequency between the labeled DNA and the unlabeled DNA. In other words, the signal produced will be weaker when the sample DNA includes a larger proportion of the sequence which is identical with the standard DNA in the target region of the sample DNA. Alternatively, the label may be introduced in one strand of the sample DNA, and in the strand of the standard DNA that is complementary to the labeled strand of the sample DNA so that a signal will be generated when the sample DNA and the standard DNA have the identical nucleotide sequence, that is, when exchange has taken place between both DNAs.

The hybridization products are measured as described above, and the identity of the sample DNA with the standard DNA, the presence/absence of mutant gene and the ratio of mutant gene to normal gene are determined from these measurements. Measurement may be done by a conventional procedure in accordance with the label used. For example, when the label is an isotope, it is only required to measure the radioactivity, and when the label is a fluorescent substance, its intensity may be directly measured by means of a fluorometer (see JP-A 252300/1989).

On the other hand, when a label other than the directly detectable label is introduced in the primer, a reagent for indirectly measuring the label is employed. When the label is biotin, a typical reagent for the indirect measurement is a complex of avidin or streptoavidin with an enzyme, and when the label is a hapten, a typical reagent is an antibody-enzyme complex comprising an antibody which specifically binds to the hapten and an enzyme bound to the hapten, and a substrate for the enzyme is also employed. The use of such a reagent allows reaction to take place between the reagent and a label to produce a component detectable by chromatic or fluorescent detection means. Exemplary combinations of enzyme and substrate which can be used for the reagent include β-D-galactosidase for the enzyme and 2-nitrophenol-β-D-galactoside, 4-methylumbelliferyl-β-D-galactoside, etc. for the substrate; peroxidase for the enzyme and 3-(4-hydroxyphenyl)propionic acid, 3,3',5,5'-tetramethylbendidine, 1,2-phenylenediamine, etc. for the substrate; alkaline phosphatase for the enzyme and 4-methylumbelliferyl phosphate, NADP, 4-nitrophenyl-phosphate, etc. for the substrate; a dehydrogenase such as gulucose-6-phosphate for the enzyme and glucose, NAD, etc. for the substrate; and alcohol dehydrogenase for the enzyme and ethanol, NAD, etc. for the substrate.

The measurement of the hybridization product as described above is carried out after trapping the hybridization product on a solid phase carrier. The solid phase carrier employed is the one which is capable of specifically binding with the solid phase carrier-binding site introduced in the primer; and a typical solid phase carrier employed is a microtiter well which has been treated to enable specific binding with the site.

With respect to the results of measurement, when the target region in the sample includes no mutation, measured values are significantly decreased because the sample DNA is diluted in the course of the measurement with the excessive amount of the labeled standard DNA. On the other hand, when the sample DNA consists solely of fragments including the mutant gene (homo), high measured values are obtained because the sample DNA is not diluted with the labeled standard DNA. When the mutation is present in half of the DNA sample (hetero; the case wherein only one of the alleles is mutant), measured values are intermediate the values measured when the mutation is absent and when the sample consists solely of fragments containing the mutant gene, and differentiation of such samples may be readily effected.

When a series of DNA samples containing fragments with mutant gene and fragments with normal gene at different ratios are measured to depict a calibration curve showing the value measured in relation to the ratio of mutant gene to normal gene, the ratio of mutant gene to normal gene in a sample may be readily determined from an actual measurement.

In the differentiation method of the present invention, even when the target nucleic acid includes the mutation site or the nucleotide sequence to be differentiated (mutation site or the like) near its primer binding site, the labeled sample DNA obtained by amplification has the mutation site or the like shifted to the central side. Accordingly, in the product resulting from hybridization of this amplification product, the double stranded fragments with no mismatch site and the double stranded fragments with mismatch site will exhibit an increased difference in stability, enabling clear differentiation of the target nucleic acid even when the mutation site or the like is located near the primer binding site.

As described above, the nucleic acid differentiation method according to Nicolas et al. comprises the steps of amplifying the DNA specimen by using a pair of primers comprising a primer having introduced therein a detectable label and a primer having introduced therein a site capable of binding to a solid phase carrier; using the resulting labeled DNA as a labeled standard DNA; adding an excessive amount of an unlabeled sample DNA to said labeled standard DNA to carry out competitive hybridization; and evaluating the hybridization product for the degree of complementary strand-exchange that has occurred between said labeled standard DNA and said unlabeled sample DNA by utilizing said detectable label and said site capable of binding to the solid phase carrier to determine the identity between the nucleic acids. In this method, the measured value will be significantly reduced for the sample in which a sequence identical with the standard DNA is present, since the labeled standard DNA would be diluted by the excessive unlabeled sample DNA; and the measured value will be high for the sample in which the identical sequence is absent, since the labeled standard DNA would not be diluted by the unlabeled sample DNA. It is then judged from a measurement value whether a fragment including the sequence identical with the labeled standard DNA is present or absent in the sample DNA.

In the present invention, the nucleic acid differentiation according to the method of Nicolas et al. is carried out by using the gene amplifying primer of the present invention that has been labeled for at least one of the primer pair for the preparation of the labeled standard DNA. When the primer of the present invention is used in the amplification of the DNA specimen wherein the site to be differentiated is located near the primer binding site, the resulting labeled standard DNA has the site for differentiation shifted to the central side, which enables reliable differentiation of the nucleic acid.

When nucleic acid differentiation is effected in accordance with the method of Nicolas et al. by using the gene amplifying primer of the present invention, the labeled standard DNA can be prepared by mixing the DNA specimen with the pair of primers wherein at least one of the primers is the gene amplifying primer of the present invention having introduced therein a detectable label and/or a site capable of binding to a solid phase carrier, and amplifying the DNA specimen. The amplification procedure of the labeled standard DNA is similar to the amplification procedure in the preparation of the labeled sample DNA in the differentiation method of the inventors of the present invention. The unlabeled sample DNA can be prepared by amplifying the particular gene to be determined in the sample using the unlabeled primer having the nucleotide sequence identical with the primer used in the preparation of the labeled standard DNA. The thus amplified gene can be further mass-produced by incorporating the gene in a vector selected from a plasmid vector, a phage vector, and a chimera vector of a plasmid and a phage, and introducing the vector in a host such as a bacteria, for example, *E. coli* or *Bacillus subtilis* or yeast (gene cloning). It is noted that when an unlabeled sample DNA is produced from a sample by amplification, the sample may be subject to pretreatment such as cell disruption, if desired, and amplification may be carried out by a conventional procedure.

Next, an equimolar amount or excess, and preferably, approximately 5 to 20 times in excess of the unlabeled sample DNA is added to the labeled standard DNA to effect competitive hybridization, and the resulting competitive hybridization product is evaluated for the degree of the complementary strand-exchange that has occurred between the labeled standard DNA and the unlabeled sample DNA by the procedure similar to the above-described differentiation method of the present inventors. It should be noted that procedures other than the above-mentioned, the reagents, members and the like used for the amplification and measurement are the same as those employed in the above-described method of the present inventors.

Next, the nucleic acid-differentiation assay kit of the present invention enables direct, rapid detection of the mutation in a nucleic acid or differentiation of genes by using the gene amplifying primer of the present invention is described. The first assay kit of the present invention is the kit for effecting assay according to the differentiation method of the present inventors, and the kit is characterized by comprising a pair of primers for preparing a labeled sample DNA comprising a primer having introduced therein a detectable label and a primer having introduced therein a site capable of binding to a solid phase carrier, wherein at least one of the primers comprises the gene amplifying primer of the present invention that has been labeled; and one of the following (A) to (C):

(A) an unlabeled DNA specimen, (B) a pair of primers for preparing an unlabeled DNA specimen wherein at least one of said primers comprises the gene amplifying primer that is unlabeled, and (C) a vector for preparing an unlabeled DNA specimen selected from a plasmid vector, a phage vector, and a chimeric vector of a plasmid and a phage.

The second assay kit of the present invention is the kit for effecting assay according to the differentiation method of Nicolas et al., and the kit is characterized by comprising a pair of primers for preparing a labeled standard DNA comprising a primer having introduced therein a detectable label and a primer having introduced therein a site capable of binding to a solid phase carrier, wherein at least one of the primers comprises the gene amplifying primer of the present invention that has been labeled; and one of the following (A) and (B):

(A) a pair of primers for preparing an unlabeled sample DNA wherein at least one of said primers comprises the gene amplifying primer of the present invention that is unlabeled, and (B) a vector for preparing an unlabeled sample DNA selected from a plasmid vector, a phage vector, and a chimeric vector of a plasmid and a phage.

When the nucleic acid differentiation assay is carried out using the above-described first kit, assay is effected in accordance with the above-described method of the present inventors, namely, by mixing the sample that has been optionally subjected to pretreatment such as cell disruption with a pair of primers including the gene amplifying primer of the present invention that has been labeled; adding amplification reagents and amplifying the sample region whose mutation is to be detected to obtain the labeled sample DNA; adding an excessive amount of the unlabeled DNA specimen or the unlabeled DNA specimen prepared with the unlabeled DNA specimen-preparing primers and the vector as the unlabeled standard DNA to effect competitive hybridization; and trapping the resulting competitive hybridization product on the carrier to evaluate the degree of strand exchange that has occurred between the DNAs.

When the nucleic acid differentiation assay is carried out by using the above-described second kit, assay is effected in accordance with the above-described method of Nicolas et al., namely, by mixing the DNA sample with a pair of the above-described labeled standard DNA-preparing primers; adding amplification reagents and amplifying the DNA to obtain the labeled standard DNA; preparing, in the meanwhile, the unlabeled sample DNA from the sample by using a pair of the unlabeled sample DNA-preparing primer or a vector; adding an excessive amount of the thus prepared unlabeled sample DNA to the labeled standard DNA to effect competitive hybridization; and trapping the resulting competitive hybridization product on the carrier to evaluate the degree of strand exchange that had occurred between the DNAS.

The amplification reagents and the carrier employed in such assay may be those known in the art, and exemplary reagents and carriers are those described in relation to the nucleic acid differentiation method of the present invention. The nucleic acid differentiation assay kit of the present invention may further comprise such reagents and carriers. The assay may be carried out by additionally employing a cell disruption reagent for sample pretreatment, a washing solution for washing the amplification product, an oil for preventing evaporation of water from the reaction solution, and reagents for indirectly detecting the label as set forth in the description of the nucleic acid differentiation method of the present invention, and the nucleic acid differentiation assay kit of the present invention may further comprise such reagents.

Next, the present invention is described in detail by referring to Examples and Comparative Examples, which by no means limit the scope of the present invention.

EXAMPLES 1 TO 3 AND COMPARATIVE EXAMPLE 1

A differentiation assay was carried out as described below in accordance with the method of Nicolas et al. to differentiate *0403 gene and *0407 gene (these genes are different only in 2 bases in a region near the primer binding site) located near the primer (DR-BAMP-B), among the genes of HLA-DRB1, which is one DR antigen of Class II antigens in the HLA antigen on sixth human chromosome. In this differentiation assay, primers of the present invention (Examples 1 to 3) and a conventional primer (Comparative Example 1) were used as a gene amplifying primer to compare the differentiation ability.

Primers

The primers used were primers DRBAMP-4 and DRBAMP-B as shown below, and primers DRBAMP-BAT, DRBAMP-BGC and DRBAMP-B4 in which an noncomplementary sequence (the underscored region) was added to the 5' end of DRBAMP-B.

DRBAMP-4 (SEQ ID NO:1)
5'-GTTTCTTGGAGCAGGTTAAAC-3'

DRBAMP-B (SEQ ID NO:2)
5'-CCGCTGCACTGTGAAGCTCT-3'

DRBAMP-BAT (SEQ ID NO:3)
5'-TTATTTATTTTATTTTTATTCCGCTGCACTGT GAAGCTCT-3'
(in the noncomplementary sequence (the underscored region) A:T:G:C=4:16:0:0)

DRBAMP-BGC (SEQ ID NO:4)
5'-CCCGCCGCGCCCCGCCCCCGCCGCTGCAC TGTGAAGCTCT-3'
(in the noncomplementary sequence (the underscored region) A:T:G:C=0:0:5:15)

DRBAMP-B4 (SEQ ID NO:5)
5'-GTAAGTGGGTAGTCTTGAGCCCGCTGCAC TGTGAAGCTCT-3'
(in the noncomplementary sequence (the underscored region) A:T:G:C=4:6:8:2)

Gene Amplification

Four pairs of amplification primers were prepared each comprising Bio-DRBAMP-4 (100 ng) having biotin introduced therein as a site capable of binding to a carrier, and one of the labeled primers DNP-DRBAMP-B, DNP-DRBAMP-BAT, DNP-DRBAMP-BGC, and DNP-DRBAMP-B4 (100 ng) having DNP introduced therein as a detectable site. To 100 µl reaction solution comprising 50 mM Tris-HCl buffer solution (pH 9.5, 25° C.), 50 mM NaCl, 10 mM $MgCl_2$ and 200 mM dNTPs were added *0407 gene together with each pair of amplification primers; and then, 2 units of Taq DNA polymerase. The reaction solution was heated to 94° C. for 5 minutes, and then subjected to 30 cycles of gene amplification each comprising heating at 94° C. for 30 seconds, 60° C. for 30 seconds and 72° C. for 1 minute (PCR). The resulting four reaction solutions were used as a labeled standard DNA solution.

In the meanwhile, other four pairs of amplification primers were prepared each comprising $NH_2$-DRBAMP-4 (100 ng), and one of the unlabeled primers $NH_2$-DRBAMP-B, $NH_2$-DRBAMP-BAT, $NH_2$-DRBAMP-BGC and $NH_2$-DRBAMP-B4 (100 ng), and *0403 gene was amplified with each pair of amplification primers in the reaction solution as described above by the PCR under the same conditions. The resulting four reaction solutions were used as an unlabeled sample DNA solution.

The amplification products in the thus produced four labeled standard DNA solutions and the four unlabeled sample DNA solutions were determined for size and production amount by agarose gel electrophoresis.

Competitive Hybridization

1 µl of the above-described labeled standard DNA solution and 20 µl of the unlabeled sample DNA solution were mixed, 6 µl of 20×SSC (20×SSC: 0.3M sodium citrate, pH 7.0; 3M sodium chloride) and 9 µl of $H_2O$ were added to this mixture, and the mixture was overlaid with mineral oil. The mixture was heated at 98° C. for 10 minutes and then gradually cooled to 68° C. at a rate of 1° C./10 minutes using a gene amplification system (Thermal Cycler PJ2000, Perkin Elmer).

The above-described procedure was repeated by preparing a reaction solution wherein 20 µl of $H_2O$ was added instead of the unlabeled sample DNA. The resulting solution was used as a control.

Detection

A 20 µl aliquot was sampled from the competitive hybridization reaction solution, and color development reaction was promoted at 25° C. for 30 minutes using ED-PCR for the detection system. Development of yellow color was measured in terms of absorbance at 405 nm to determine the amount of the residual double stranded DNA having both the biotin and DNP labels. The competitive hybridization procedure as described above was simultaneously conducted in two test tubes, and the measurements were averaged.

Evaluation

From the thus obtained results, the dilution index (the degree of dilution of the labeled standard DNA (*0407 gene) with the unlabeled sample DNA (*0403 gene)) was calculated by dividing the absorbance at 405 nm of the reaction solution wherein the unlabeled sample DNA was added to the labeled sample DNA by the absorbance at 405 nm of the reaction solution wherein $H_2O$ was added instead of the unlabeled sample DNA. The results are shown in Table 1, below.

EXAMPLES 4 TO 6 AND COMPARATIVE EXAMPLE 2

A differentiation assay was carried out as described below in accordance with the method of Nicolas et al. to differentiate *1301 gene and *1302 gene which are different from one another only by 2 bases in a region near the primer binding site, among the genes of HLA-DRB1. In this differentiation assay, primers of the present invention (Examples 4 to 6) and a conventional primer (Comparative Example 2) were used as a gene amplifying primer to compare the differentiation ability.

Primers

The primers used were primers DRBAMP-3/5/6 and DRBAMP-B whose base composition is shown below, and primers DRBAMP-BAT, DRBAMP-BGC and DRBAMP- B4 in which a noncomplementary sequence (the underscored region) was added to the 5' end of DRBAMP-B.

DRBAMP-3/5/6 (SEQ ID NO:6)
5'-TTCTTGGAGTACTCTACGTC-3'

DRBAMP-B (SEQ ID NO:2)
5'-CCGCTGCACTGTGAAGCTCT-3'

DRBAMP-BAT (SEQ ID NO:3)
5'-TTATTTATTTTATTTTTATTCCGCTGCACTGTGAAGCTCT-3'
(in the noncomplementary sequence (the underscored region) A:T:G:C=4:16:0:0)

DRBAMP-BGC (SEQ ID NO:4)
5'-CCCGCCGCGCCCCGCCCCCGCCGCTGCACTGTGAAGCTCT-3'
(in the noncomplementary sequence (the underscored region) A:T:G:C=0:0:5:15)

DRBAMP-B4 (SEQ ID NO:5)
5'-GTAAGTGGGTAGTCTTGAGCCCGCTGCACTGTGAAGCTCT-3'
(in the noncomplementary sequence (the underscored region) A:T:G:C=4:6:8:2)

Gene Amplification

Four pairs of amplification primers were prepared each comprising Bio-DRBAMP-3/5/6 (100 ng) having biotin introduced therein as a site capable of binding to a carrier, and one of the labeled primers DNP-DRBAMP-B, DNP-DRBAMP-BAT, DNP-DRBAMP-BGC and DNP-DRBAMP-B4 (100 ng) having DNP introduced therein as a detectable site. *1301 gene was added to 100 μl reaction solution comprising 50 mM Tris-HCl buffer solution (pH 9.5, 25° C.), 50 mM NaCl, 10 mM $MgCl_2$ and 200 mM dNTPs together with each pair of amplification primers; and then, 2 units of Taq DNA polymerase added. The reaction solution was heated to 94° C. for 5 minutes, and then, subjected to 30 cycles of gene amplification each comprising heating at 94° C. for 30 seconds, 60° C. for 30 seconds and 72° C. for 1 minute (PCR). The resulting four reaction solutions were used as a labeled standard DNA solution.

In the meanwhile, other four pairs of amplification primers were prepared each comprising $NH_2$-DRBAMP-3/5/6 (100 ng), and one of the unlabeled primers $NH_2$-DRBAMP-B, $NH_2$-DRBAMP-BAT, $NH_2$-DRBAMP-BGC and $NH_2$-DRBAMP-B4 (100 ng), and *1302 gene was amplified with each pair of amplification primers in the reaction solution as described above by the PCR under the same conditions. The resulting four reaction solutions were used as an unlabeled sample DNA solution.

The amplification products in the thus produced four labeled standard DNA solutions and the four unlabeled sample DNA solutions were determined for size and production amount by agarose gel electrophoresis.

Competitive Hybridization

1 μl of the above-described labeled standard DNA solution and 20 μl of the unlabeled sample DNA solution were mixed, 6 μl of 20×SSC (20×SSC: 0.3M sodium citrate, pH 7.0; 3M sodium chloride) and 9 μl of $H_2O$ were added to this mixture, and the mixture was overlaid with mineral oil. The mixture was heated at 98° C. for 10 minutes and then gradually cooled to 68° C. at a rate of 1° C./10 minutes using a gene amplification system (Programmable thermal controller, MJ Research).

The above-described procedure was repeated by preparing a reaction solution wherein 20 μl of $H_2O$ had been added instead of the unlabeled sample DNA. The resulting solution was used as a control.

Detection

A 20 μl aliquot was sampled from the competitive hybridization reaction solution, and color development reaction was promoted at 25° C. for 30 minutes using ED-PCR for the detection system. Development of yellow color was measured in terms of absorbance at 405 nm to determine the amount of the residual double stranded DNA having both the biotin and DNP labels. The competitive hybridization procedure as described above was simultaneously conducted in two test tubes, and the measurements were averaged.

Evaluation

From the thus obtained results, the dilution index (the degree of dilution of the labeled standard DNA (*1301 gene) with the unlabeled sample DNA (*1302 gene)) was calculated by dividing the absorbance at 405 nm of the reaction solution wherein the unlabeled sample DNA was added to the labeled sample DNA by the absorbance at 405 nm of the reaction solution wherein $H_2O$ was added instead of the unlabeled sample DNA. The results are shown in Table 2, below.

TABLE 1

|  | Comparative Example | Example | | |
|---|---|---|---|---|
|  | 1 | 1 | 2 | 3 |
| Primers | DRBAMP-4 | DRBAMP-4 | DRBAMP-4 | DRBAMP-4 |
|  | DRBAMP-B | DRBAMP-BAT | DRBAMP-B4 | DRBAMP-BGC |
| Dilution index | 0.087 | 0.088 | 0.103 | 0.122 |

TABLE 2

|  | Comparative Example | Example | | |
|---|---|---|---|---|
|  | 2 | 4 | 5 | 6 |
| Primers | DRBAMP-3/5/6 | DRBAMP-3/5/6 | DRBAMP-3/5/6 | DRBAMP-3/5/6 |
|  | DRBAMP-B | DRBAMP-BAT | DRBAMP-B4 | DRBAMP-BGC |
| Dilution index | 0.171 | 0.172 | 0.236 | 0.436 |

The results of Tables 1 and 2 indicate that the use of primers of the present invention (DRBAMP-BAT, DRBAMP-B4 and DRBAMP-BGC) (Examples 1 to 6) results in higher values of dilution index than the use of the conventional primer (DRBAMP-B) (Comparative Examples 1 and 2), and the dilution index value increases in this order, indicating the preferential formation of a homoduplex to a heteroduplex. As described above, the use of the primer of the present invention having a sequence noncomplementary to the target nucleic acid added thereto enables the preferential formation of a homoduplex and hence, clear differentiation. Addition of the noncomplementary sequence solely comprising the bases of G and C (DRBAMP-BGC, Examples 3 and 6) showed most significant effects.

EXAMPLE 7 AND COMPARATIVE EXAMPLE 3

Using a primer of the present invention and a conventional primer, a sample of DRB1 *1301/*1301 (homo) and a sample of DRB1 *1301/*1402 (hetero) were differentiated in accordance with the method of Nicolas et al. using a labeled standard DNA and an unlabeled sample DNA.

Sample 1 (DRB1 *1301/*1301) and sample 2 (DRB1 *1301/*1402) were amplified under the conditions similar to the above-described Examples 4 to 6 using the primer pair comprising $NH_2$-DRBAMP-3/5/6, and either one of $NH_2$-DRBAMP-B (conventional primer) and $NH_2$-DRBAMP-BGC (inventive primer), obtaining the unlabeled sample DNA.

The labeled standard DNA was produced by amplifying respective genes of the DNA sample shown in Table 3 with the amplification primer pair comprising Bio-DRBAMP-3/5/6, and either one of DNP-DRBAMP-B (conventional primer) and DNP-DRBAMP-BGC (inventive primer).

1 μl of each of the labeled standard DNA was mixed with 20 μl of each of the unlabeled sample DNA, and competitive hybridization was carried out by repeating the procedure of Examples 4 to 6 as described above. The amount of the remaining DNA having both biotin and DNP labels was measured. The results are shown in Table 3. It should be noted that the results are shown in the Table only the major ones of the labeled standard DNA used. The values shown in the Table are the proportion of the labeled standard DNA that was diluted by the unlabeled sample DNA, namely, the dilution index.

As seen from the results of Table 3, sample 2 exhibited a low absorbance for the labeled standard DNAs *1301, *1302 and *1402 when the conventional primer (Comparative Example 3) was used. Such results are based on the fact that the conventional primer is difficult to differentiate *1301 and *1302, whose only difference is the 2 bases located near the primer binding site. In contrast, when the inventive primer (Example 7) was used, sample 2 exhibited a low value only for *1301 and *1402, confirming that the sample 2 is a hetero having the genotypes of *1301 and *1402.

With regard to sample 1, this sample exhibited a low value for the labeled standard DNAs *1301 and *1302 when the conventional primer was used. This sample, however, exhibited a low value only for *1301 when the inventive primer was used, and the presence of the *1302 gene was thus denied.

As demonstrated in the foregoing, the gene amplifying primer of the present invention enables nucleic acid differentiation at a higher accuracy than the conventional primer.

EXAMPLE 8 AND COMPARATIVE EXAMPLE 4

In Example 7, the presence of *1302 could be denied for sample 1 as described above. The results of Table 3 also confirmed the presence of *1301 in sample 1. The procedure of Example 7, however, could not differentiate whether sample 1 was a *1301 homo or a hetero with a gene other than the one examined in that Example. In view of such situation, second stage typing was carried out in accordance with the differentiation method of the present inventors wherein the sample is amplified with the labeled primer to prepare the labeled sample DNA; and an excessive amount of unlabeled standard DNA is added to the labeled sample DNA to effect the competitive hybridization. In this differentiation method, when the labeled sample DNA is a homo of the type of the unlabeled standard DNA, the molecule having the label on its opposite ends will finally be reduced at an arithmetic dilution index, and the absorbance will be about 1/20 of the initial value. On the contrary, when the labeled sample DNA has one allele which is of different type (hetero), it is theoretically expected that half the amount of the labeled sample DNA molecule derived from the chromosomal DNA of the same type as the unlabeled standard DNA will be arithmetically diluted to provide little contribution to absorbance, while the other half will not undergo a substantial dilution, and as a result, the absorbance is about ½ of the initial absorbance. The following assay was conducted in accordance with this principle.

Sample 1 as described above was amplified under conditions similar to the above-described conditions using a pair of amplifying primers comprising Bio-DRBAMP-3/5/6 and either one of DNP-DRBAMP-B (conventional primer) and DNP-DRBAMP-BGC (inventive primer). For ease of comparison, a specimen solely comprising *1301 gene (homo) and a specimen comprising a mixture of *1301 and *1302 (hetero) were also amplified under the same conditions. The amplified products were used as labeled sample DNAs.

The genes DRB1 *1301, *1302, *1402, and *1405 were amplified with a pair of amplification primers comprising $NH_2$-DRBAMP-3/5/6 and either one of $NH_2$-DRBAMP-B (conventional primer) and $NH_2$-DRBAMP-BGC (inventive primer), obtaining unlabeled standard DNAS.

1 μl of the labeled sample DNA was mixed with 20 μl of the unlabeled standard DNA, and competitive hybridization was carried out under conditions similar to the above-described conditions. The amount of the remaining DNA having both the biotin and the DNP labels was measured. The results are shown in Table 4. It should be noted that the values shown in the Table are the proportion of the labeled sample DNA that was diluted by the unlabeled standard DNA, namely, the dilution index.

TABLE 3

| Unlabeled sample | Labeled standard DNA | | | | | | | |
|---|---|---|---|---|---|---|---|---|
| | Conventional primer Comparative Example 3 | | | | Inventive primer Example 7 | | | |
| DNA | *1301 | *1302 | *1402 | *1405 | *1301 | *1302 | *1402 | *1405 |
| Sample 1 | 0.07 | 0.12 | 0.83 | 0.85 | 0.08 | 0.42 | 0.83 | 0.88 |
| Sample 2 | 0.09 | 0.14 | 0.10 | 0.83 | 0.10 | 0.43 | 0.11 | 0.89 |

TABLE 4

| Labeled sample | Unlabeled standard DNA | | | | | | | |
|---|---|---|---|---|---|---|---|---|
| | Conventional primer Comparative Example 4 | | | | Inventive primer Example 8 | | | |
| DNA | *1301 | *1302 | *1402 | *1405 | *1301 | *1302 | *1402 | *1405 |
| Sample 1 | 0.08 | 0.15 | 0.85 | 0.90 | 0.07 | 0.45 | 0.83 | 0.88 |
| 1301/1301 (homo specimen) | 0.07 | 0.14 | 0.85 | 0.90 | 0.07 | 0.48 | 0.88 | 0.91 |
| 1301/1302 (hetero specimen) | 0.10 | 0.12 | 0.88 | 0.86 | 0.21 | 0.24 | 0.90 | 0.89 |

As seen from the results of Table 4, in the case wherein the conventional primer was used, the *1301/*1301 homo specimen and the *1301/*1302 hetero specimen exhibited dilutions which were not significantly different from each other. In contrast, when the inventive primer was used, the *1301/*1301 homo specimen and the *1301/*1302 hetero specimen could be clearly differentiated (Example 8). Furthermore, since the sample 1 exhibited a dilution pattern similar to that of the *1301 homo specimen, the sample 1 was confirmed to be a *1301 homo.

As demonstrated in the foregoing, the nucleic acid differentiation in accordance with the method of the present inventors using the primer of the present invention enables reliable differentiation even when the mutation site or the like to be differentiated is located near the primer binding site, as well as convenient differentiation between the homo and the hetero.

As described above, when a target nucleic acid has a mutation site or nucleotide sequence to be differentiated (mutation site or the like) located near its primer binding site, the gene amplifying primer of the present invention produces an amplification product wherein the mutation site or the like has shifted to the central side. When nucleic acid differentiation by competitive hybridization utilizing complementary strand-exchange reaction is carried out using the thus amplified product, the target nucleic acid can be readily differentiated.

In addition, the nucleic acid differentiation method of the present invention enables clear, easy differentiation of a nucleic acid even when the target nucleic acid includes the mutation site or the like near its primer binding site.

Furthermore, the nucleic acid differentiation assay kit of the present invention enables nucleic acid differentiation assay to be readily and reliably carried out in accordance with the differentiation method of the present invention as described above.

We claim:

1. A nucleic acid identification method for identifying a gene in a selected region of a target nucleic acid in a sample, comprising the steps of:

amplifying the selected region of the target nucleic acid in the sample by using a pair of a first primer having introduced therein a detectable label and a second primer having introduced therein a site capable of binding to a solid phase carrier, at least one of said primers being a gene amplifying primer comprising a primer main region which is complementary to a target nucleic acid to be amplified and a noncomplementary sequence having from 10 to 40 bases added to the 5' end of the primer main region which is noncomplementary to the target nucleic acid to produce a labeled DNA;

using the resulting labeled DNA as a labeled sample DNA and using an unlabeled DNA specimen to be determined for identity with said labeled sample DNA as an unlabeled standard DNA;

adding at least an equimolar amount of said unlabeled standard DNA to said labeled sample DNA to carry out competitive hybridization; and thereafter measuring the degree of complementary strand-exchange that has occurred between said labeled sample DNA and said unlabeled standard DNA by utilizing said detectable label and said site capable of binding to the solid phase carrier, to thereby determine the identity of the nucleic acids.

2. The nucleic acid identification method according to claim 1 wherein said unlabeled standard DNA has been prepared using a pair of primers, at least one of which is said gene amplifying primer.

3. The nucleic acid identification method according to claim 1 wherein said unlabeled standard DNA has been prepared by gene cloning using a vector selected from a plasmid vector, a phage vector, and a chimeric vector of plasmid and phage.

4. A nucleic acid identification assay kit for effecting nucleic acid identification according to the method of claim 1, said kit comprising:

a pair of primers for preparing a labeled sample DNA comprising a first primer having introduced therein a detectable label and a second primer having introduced therein a site capable of binding to a solid phase carrier, at least one of the primers being a gene amplifying primer comprising a primer main region which is complementary to a target nucleic acid to be amplified and a noncomplementary sequence having from 10 to 40 bases added to the 5' end of the primer main region which is noncomplementary to the target nucleic acid; and one of the following (A) to (C):

(A) an unlabeled DNA specimen, (B) a pair of primers for preparing an unlabeled DNA specimen, at least one of said primers being said gene amplifying primer, and (C) a vector for preparing an unlabeled DNA specimen selected from a plasmid vector, a phage vector, and a chimeric vector of plasmid and phage.

5. A nucleic acid identification method for identifying a gene in a selected region of a target nucleic acid in a sample, comprising the steps of:

amplifying a DNA specimen using a pair of a first primer having introduced therein a detectable label and a second primer having introduced therein a site capable of binding to a solid phase carrier, at least one of said primers being a gene amplifying primer comprising a primer main region which is complementary to a target nucleic acid to be amplified and a noncomplementary sequence having from 10 to 40 bases added to the 5' end of the primer main region which is noncomplementary to the target nucleic acid to produce a labeled DNA;

using the resulting labeled DNA as a labeled standard DNA and using an unlabeled DNA to be determined for identity with the labeled standard DNA in the selected region of the target nucleic acid in the sample as an unlabeled sample DNA;

adding at least an equimolar amount of said unlabeled sample DNA to said labeled standard DNA to carry out competitive hybridization; and thereafter measuring the degree of complementary strand-exchange that has occurred between said labeled standard DNA and said unlabeled sample DNA by utilizing said detectable label and said site capable of binding to the solid phase carrier, to thereby determine the identity of the nucleic acids.

6. The nucleic acid identification method according to claim 5 wherein said unlabeled sample DNA has been prepared using a pair of primers at least one of which is said gene amplifying primer.

7. The nucleic acid identification method according to claim 5 wherein said unlabeled sample DNA has been prepared by gene cloning using a vector selected from a plasmid vector, a phage vector, and a chimeric vector of plasmid and phage.

8. A nucleic acid identification assay kit for effecting nucleic acid identification according to claim 5, said kit comprising:

a pair of primers for preparing a labeled standard DNA comprising a first primer having introduced therein a detectable label and a second primer having introduced therein a site capable of binding to a solid phase carrier, at least one of the primers being a gene amplifying primer comprising a primer main region which is complementary to a target nucleic acid to be amplified and a noncomplementary sequence having 10 to 40 bases added to the 5' end of the primer main region which is noncomplementary to the target nucleic acid; and one of the following (A) and (B):
- (A) a pair of primers for preparing an unlabeled sample DNA, at least one of said primers being said gene amplifying primer, and
- (B) a vector for preparing an unlabeled sample DNA selected from a plasmid vector, a phage vector, and a chimeric vector of plasmid and phage.

9. The nucleic acid identification assay kit according to claim 4, comprising:

reagents for amplifying a gene in a selected region of a target nucleic acid in a sample;

a carrier for trapping the hybridization product of said competitive hybridization; and a reagent for detecting the trapped hybridization product.

10. The nucleic acid identification assay kit according to claim 8, comprising:

reagents for amplifying a gene in a selected region of a target nucleic acid in a sample;

a carrier for trapping the hybridization product of said competitive hybridization; and a reagent for detecting the trapped hybridization product.

11. The nucleic acid identification method according to claim 1, wherein the bases of said noncomplementary sequence comprise at least 50% of guanine (G) and/or cytosine (C).

12. The nucleic acid identification method according to claim 5, wherein the bases of said noncomplementary sequence comprise at least 50% of guanine (G) and/or cytosine (C).

13. The nucleic acid identification assay kit according to claim 4, wherein the bases of said noncomplementary sequence comprise at least 50% of guanine (G) and/or cytosine (C).

14. The nucleic acid identification assay kit according to claim 8, wherein the bases of said noncomplementary sequence comprise at least 50% of guanine (G) and/or cytosine (C).

* * * * *